US007462227B2

(12) United States Patent
Anderson et al.

(10) Patent No.: US 7,462,227 B2
(45) Date of Patent: Dec. 9, 2008

(54) IBUPROFEN COMPLEXES AS WOOD PRESERVATIVES

(75) Inventors: Albert Gordon Anderson, Wilmington, DE (US); John Feaster, Chesapeake City, MD (US); Damini Patel, Wallingford, PA (US); Mark Scialdone, West Grove, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 34 days.

(21) Appl. No.: 11/643,599

(22) Filed: Dec. 21, 2006

(65) Prior Publication Data

US 2007/0169664 A1 Jul. 26, 2007

Related U.S. Application Data

(60) Provisional application No. 60/755,214, filed on Dec. 30, 2005.

(51) Int. Cl.
*A01N 59/16* (2006.01)
*A01N 59/20* (2006.01)
*A01N 31/00* (2006.01)
*B05D 5/00* (2006.01)
*B05D 7/06* (2006.01)
*B05D 1/02* (2006.01)
*B05D 1/18* (2006.01)
*B05D 1/28* (2006.01)
*B05D 3/00* (2006.01)
*B32B 21/04* (2006.01)
*B32B 21/06* (2006.01)

(52) U.S. Cl. .............. 106/15.05; 106/18.36; 252/399; 252/400.1; 252/400.52; 252/400.54; 252/405; 252/407; 424/78.08; 424/78.09; 424/405; 424/638; 427/297; 427/351; 427/421.1; 427/428.01; 427/429; 427/439; 427/440; 428/375; 428/532; 428/537.1; 428/537.5; 514/492; 514/494; 514/500; 514/557; 514/568; 514/570; 514/784

(58) Field of Classification Search .............. 106/15.05, 106/18.36; 252/399, 400.1, 400.52, 400.54, 252/405, 407; 424/78.08, 78.09, 405, 638; 427/297, 351, 421.1, 428.01, 429, 439, 440; 428/375, 532, 537.1, 537.5; 514/492, 494, 514/500, 557, 568, 570, 784
See application file for complete search history.

(56) References Cited

U.S. PATENT DOCUMENTS

| 3,404,135 | A | 10/1968 | Tietz |
| 3,706,704 | A | 12/1972 | Heilman |
| 4,175,090 | A | 11/1979 | Berry |
| 4,409,358 | A | 10/1983 | Kraft et al. |
| 4,504,468 | A | 3/1985 | Brill et al. |
| 4,656,192 | A | 4/1987 | Yamato |
| 4,737,491 | A | 4/1988 | Leppavuori et al. |
| 4,988,545 | A | 1/1991 | Laks |
| 5,242,685 | A | 9/1993 | Ruppersberger et al. |
| 6,197,763 | B1 | 3/2001 | Thompson et al. |
| 6,541,038 | B1 | 4/2003 | Tanaka et al. |
| 6,787,675 | B2 | 9/2004 | Pan et al. |
| 6,843,837 | B2 | 1/2005 | Zhang et al. |
| 6,924,398 | B2 | 8/2005 | Pan et al. |
| 6,978,724 | B2 * | 12/2005 | Anderson et al. ......... 106/18.32 |
| 7,259,187 | B2 | 8/2007 | Kagechika |
| 2004/0089196 | A1 | 5/2004 | Anderson et al. |
| 2005/0000387 | A1 | 1/2005 | Wang et al. |
| 2005/0107467 | A1 | 5/2005 | Richardson |
| 2007/0157847 | A1 * | 7/2007 | Anderson et al. ......... 106/18.32 |
| 2007/0163465 | A1 * | 7/2007 | Anderson et al. ............. 106/12 |
| 2007/0163466 | A1 * | 7/2007 | Anderson et al. ......... 106/18.32 |
| 2007/0169664 | A1 * | 7/2007 | Anderson et al. ......... 106/18.32 |

FOREIGN PATENT DOCUMENTS

| AU | 614386 | 8/1991 |
| EP | 0 728 478 | 8/1968 |
| EP | 0 111 995 A2 | 6/1984 |
| EP | 0 137 126 | 4/1985 |
| EP | 238 413 | 9/1987 |
| EP | 0 565 266 | 10/1993 |
| FR | 2 668 031 | 4/1992 |
| JP | 1299291 A | 12/1989 |
| JP | 02/006402 | 1/1990 |
| JP | 7-069825 A | 3/1995 |
| JP | 7-126111 A | 5/1995 |
| JP | 8-12504 | 1/1996 |
| JP | 10291205 A | 4/1997 |
| JP | 9-175916 | 7/1997 |
| JP | 09175916 | 7/1997 |
| JP | 10-45518 A | 2/1998 |
| JP | 2000/141316 | 5/2000 |
| JP | 2001/097808 | 4/2001 |
| JP | 2001-310302 A | 11/2001 |

(Continued)

OTHER PUBLICATIONS

U.S. Appl. No. 60/755,211, filed Dec. 30, 2005, Anderson.*
U.S. Appl. No. 60/755,213, filed Dec. 30, 2005, Anderson.*
U.S. Appl. No. 60/755,214, filed Dec. 30, 2005, Anderson.*
U.S. Appl. No. 60/755,242, filed Dec. 30, 2005, Anderson.*
U.S. Appl. No. 60/014,812, filed Dec. 19, 2007, Anderson et al.*
U.S. Appl. No. 60/014,820, filed Dec. 19, 2007, Anderson et al.*
U.S. Appl. No. 60/014,827, filed Dec. 19, 2007, Anderson et al.*
U.S. Appl. No. 60/014,830, filed Dec. 19, 2007, Anderson et al.*
U.S. Appl. No. 60/014,841, filed Dec. 19, 2007, Anderson et al.*
W.J. Brill et al., "Termite Killing By Molybdenum and Tungsten Compounds," Naturwissenschaften, vol. 74:494-495 (1987). [no month].

(Continued)

Primary Examiner—Anthony J. Green

(57) ABSTRACT

Complexes of ibuprofen and copper and/or zinc were solubilized in ammoniacal solution providing preservative solutions that fully penetrate wood. With loss of the ammonia from the wood, the complexes were stably retained in the wood providing a long lasting preservative.

28 Claims, No Drawings

FOREIGN PATENT DOCUMENTS

| | | |
|---|---|---|
| JP | 2003137702 | 5/2003 |
| JP | 2003-334804 A | 11/2003 |
| JP | 2004-043327 A | 2/2004 |
| JP | 49055829 A | 4/2005 |
| JP | 01038203 A | 1/2006 |
| WO | WO 97/15382 | 5/1997 |
| WO | WO 00/19827 | 4/2000 |
| WO | WO 2004/041491 | 5/2004 |

OTHER PUBLICATIONS

Connick et al. "Enviromental Entomology", vol. 30, pp. 449-455. [no date].

Carol A. Clausen: Report #IRG/WP 96-10160: "Ibuprofen Inhibits In Vitro Growth of Brown-Rot Fungi" International Research Group on Wood Preservation, Stockholm, Sweden (1996) [no month].

A. Trinchero et al., "Spectroscopic Behavior of Copper Complexes of Non-Steroidal Antiflammatory Drugs" Biopolymers, vol. 74, pp. 120-124 (2004) [no month].

S. Dutta et al., "Structural Characterization and Sod Activity of Copper-Oxaprozinate," Inorganic Chemistry Communications, Elsevier, Amsterdam, NL, vol. 7, No. 9, pp. 1071-1074 (Sep. 2004).

International Search Report, Application No. PCT/US2006/049543, Written Opinion of the International Searching Authority (Jul. 18, 2007).

International Search Report, Application No. PCT/US2006/049541, Written Opinion of the International Searching Authority (Aug. 20, 2007).

International Search Report, Application No. PCT/US2006/049544, Written Opinion of the International Searching Authority (Dec. 28, 2006).

International Search Report, Application No. PCT/US2006/049542, Written Opinion of the International Searching Authority (Aug. 15, 2007).

Mounir Baya et al., "Fungicidal Activity of Beta-Thujaplicin Analogues," Pest Management Science, vol. 57, pp. 833-838 (2001). [no month].

John M. Black, "inorganic Surface Treatments for Weather Resistant Natural Finishes," U.S.D.A. Forrest Service Research Paper 174, vol. 232, p. 40 (1974). [no month].

Jennifer Cowan et al., "Leaching studies and fungal resistance of potential new wood preservatives," Institute of Technology and School of Chemical and Biomolecular Engineering, Georgia Institute of Technology, Article No. 9796 (2003). [no month].

* cited by examiner

IBUPROFEN COMPLEXES AS WOOD PRESERVATIVES

This application claims the benefit of U.S. Provisional Application No. 60/755,214, which is incorporated in its entirety as a part hereof for all purposes.

TECHNICAL FIELD

This invention relates to preservatives for wood and other cellulosic materials. Specifically, protection of cellulosic materials is provided by the application of solutions of ibuprofen complexed with copper or zinc ions. These complexes readily penetrate the cellulosic materials.

BACKGROUND

The decay of wood and other cellulosic materials by fungi, and the consumption of wood by termites, cause significant economic loss. Until recently, the most widely used wood preservative has been chromated copper arsenate (CCA). However, production of CCA for use in residential structures was prohibited as of January 2004 due to issues raised concerning the environmental impact and safety of arsenic and chromium used in CCA-treated lumber. As CCA replacements, arsenic-free and chromium-free wood preservatives are sought. Retention in treated wood of copper and other metal ions that are effective fungicides is a challenge. Metal salts are generally water soluble and rapidly leach from treated wood, which causes loss of the preservative function.

Wood rotting fungi are typically either white-rot or brown-rot basidiomycetes. Brown-rot fungi are the most destructive wood rotting organisms, though they make up only 7% of all wood rotting basidiomycetes (Gilbertson and Ryvarden (1986) North American Polypores, Abortiporus-Lindtneria, Vl. Gronslands Grafiske A/S, Olso, Norway). The brown-rot fungi are generally tolerant of copper, the typically used wood preservative, which is effective against the white-rot fungi. Thus, compounds active against brown-rot fungi are needed in wood preservatives.

Ibuprofen has been shown to be toxic to many different isolates of brown-rot fungi [Clausen, Report #IRG/WP 10160, (1996) USDA Forest Products Lab., Madison, Wis.]. In addition, ibuprofen has been found to be toxic to termites (Connick et al, (2001) Environmental Entomology, v 30, p 449-455). The potential value of ibuprofen as a wood preservative, however, would be limited by the fact that is only slightly soluble in water, so solutions with effective wood preservative concentrations cannot be readily made.

Thus there is a need for ibuprofen-containing wood preservatives that can penetrate wood, and yet be fixed in the wood to provide long-term protection.

SUMMARY

One embodiment of this invention provides an aqueous composition comprising in admixture (a) a complex comprising (i) ibuprofen, and (ii) copper ions, zinc ions or a mixture thereof; and (b) ammonia and/or ethanolamine; wherein component (b) is present in an amount sufficient to solubilize the complex.

Another embodiment of this invention provides a process for preparing a composition by combining the components (a) and (b) described above, and solubilizing a complex as formed therefrom.

A further embodiment of this invention provides a process for preserving a cellulosic material, or an article that comprises a cellulosic material, comprising contacting the cellulosic material or the article with the composition described above.

Yet another embodiment of this invention provides a cellulosic material, or an article comprising a cellulosic material, wherein the above described composition is adsorbed on or absorbed in the cellulosic material.

DETAILED DESCRIPTION

A complex that is formed from ibuprofen, and copper and/or zinc ions, is solubilized by, for example, ammonia or ethanol amine, and is used in such form as a deeply-penetrating and long lasting preservative for wood and other cellulosic materials. As the metal ion complex is solubilized in an aqueous medium, it can be readily adsorbed onto, and/or absorbed or imbibed into, wood or other cellulosic materials. Upon loss or evaporation of the solvent or co-solvents in the solution, the complex becomes insoluble, thereby fixing the ibuprofen and the metal ion(s) within the target material, and providing an effective preservative composition for the cellulosic material.

A cellulosic material is preserved in the sense that contact with a composition of this invention protects the material against decay or deterioration from deleterious effects as caused by either or both of pests and living organisms. Resistance to brown-rot fungi is imparted to the cellulosic materials due to the brown-rot fungicidal activity of ibuprofen, and white-rot fungal protection is imparted due to the copper and/or zinc ions. The termiticidal activity of ibuprofen also aids in preservation of the cellulosic materials. The potential for deterioration or destruction of a cellulosic material by exposure to natural conditions or hazards is thus reduced and preferably prevented by the presence in and/or on the material of a composition of this invention. A process of this invention provides preservation for cellulosic materials by providing contact of the materials with a composition of this invention, and thus achieves the benefits of protection against adverse conditions, pests and organisms, such as termites and fungi as described above.

The cellulosic materials that can be treated with a composition of this invention are those that contain or are derived from cellulose, which is a polysaccharide that forms the main constituent of the cell wall in most plants, and is thus the chief constituent of most plant tissues and fibers. These cellulosic materials include wood and wood products such as lumber, plywood, oriented strand board and paper, in addition to lignin, cotton, hemicellulose and cellulose itself. References herein to the preservation of wood by the use of a composition of this invention, or by the performance of a process of this invention, or references to the usefulness of a composition hereof as a wood preservative, should therefore be understood to be references to the preservation of all types of cellulosic materials, not just wood alone.

Ibuprofen with Copper/Zinc in Solution

Ibuprofen used to prepare preservative solutions of this invention may be supplied as ibuprofen or sodium ibuprofenate. These compounds are soluble in methanol and ethanol but relatively insoluble in water.

The fungitoxic metals copper and zinc, in ionic state, e.g. copper ion, may be used to form complexes with ibuprofen that are solubilized in order to provide a preservative composition according to this invention. Any soluble copper salt may be a source of copper ions, for example, Cu(II) salts may include copper sulfate, copper sulfate pentahydrate, cupric chloride, cupric acetate, and copper carbonate. Particularly useful as the copper salt is copper sulfate pentahydrate. Any soluble zinc salt may be a source of zinc ions, for example Zn(II) salts may include zinc sulfate, zinc chloride, zinc acetate, zinc nitrate, and zinc carbonate. Particularly useful as the zinc salt is zinc acetate. Mixtures of copper ion sources and zinc ion sources may be used in the compositions of this invention as well. Sources of ibuprofen, and copper ions and zinc ions, as described above, are available commercially.

To form a composition of this invention, the components thereof are combined in admixture. For example, an aqueous solution may be prepared that contains ibuprofen or an ibuprofen salt, and a copper and/or zinc salt or other source of copper ions. The mixture in solution of the components as described above forms a complex. A complex as used herein is essentially a salt, but may also be described as an association containing organic and/or inorganic components in any combination that is held together by covalent or electrostatic bonds, or by bonds that are intermediate between covalent and electrostatic bonds such as in a coordination compound. One example of the combination of components as mentioned above leads to formation of a complex between an ibuprofenate and a copper ion, and the complex precipitates in aqueous solution, as shown in Diagram I. Shown is a simplified diagram. The structure of the copper complex can be found in Trinchero et al, Biopolymers (2004) 74, p 120-124.

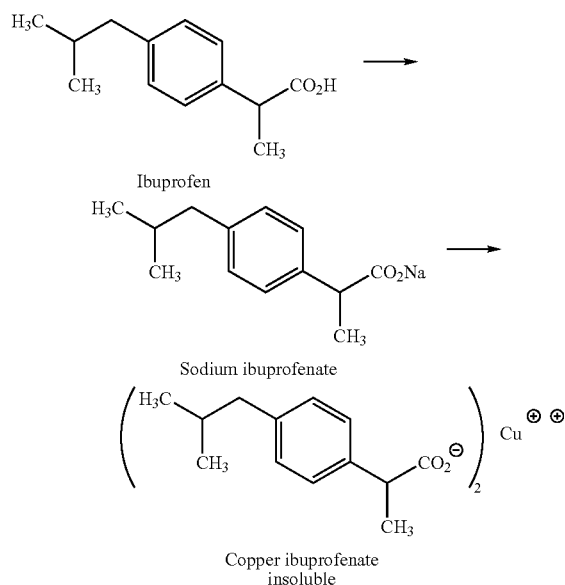

By combining these components in an aqueous ammoniacal solution, the ibuprofenate and metal ion complex was found to remain fully soluble as shown in Diagram II:

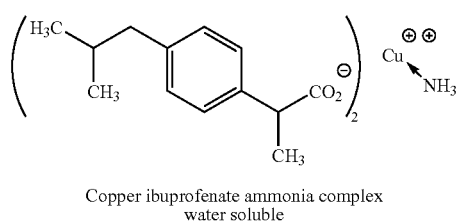

In preparing this solution, it is particularly useful to include ammonium hydroxide in sufficient concentration to preclude the formation of a precipitate while mixing the components. A solvent or co-solvent such as ammonia is present in sufficient amount to maintain solubility of the complex in the aqueous mixture. Typically, ammonia as used to prepare the solution is used in an amount such that it is present at about 0.5% to 3% by weight in the final solution. Preferred is 1.4 wt % ammoniacal water solution. Ethanolamine may be used in an amount of about 0.5% to 3% by weight of the solution as an alternative to ammonia. Additionally, combinations of ethanolamine and ammonia may be used. Although use of ammonia is preferred, other solvents or co-solvents that form a solution with water, that solubilize the complex as readily as ammonia, and also evaporate as readily as ammonia from the cellulosic material after treatment, may also be used in addition to or in place of ammonia or ethanol amine in the solvent system in which the complex is solubilized.

In general, solubility of the complex is determined by visual observation, and a complex is considered to be solbilized when a sufficient amount of the complex is dissolved in the solution to permit a desired amount of the complex to be adsorbed on and/or absorbed in the cellulosic material when the treatment thereof occurs.

Mixtures of ibuprofen with copper and/or zinc ions are used in the preservative compositions of this invention in amounts effective to provide a desired level of protection in view of the service conditions (including the nature of the target material, the contemplated end use, and the geographic location) that the cellulosic material to be treated will experience. The concentration of ibuprofen in the treatment solution is thus usually in the range of about 100 to about 20,000 ppm, or in the range of between about 100 to about 1,000 ppm, or in the range of between about 200 to about 700 ppm, or in the range of about 300 to about 500 ppm. The copper and/or zinc ions are typically used at a concentration in the treatment solution in the range of about 500 ppm to about 11,000 ppm. Marine use generally requires the higher concentrations, up to about 11,000 ppm while land use may involve concentrations between about 500 and 6,000 ppm. It is particularly useful to include corresponding amounts of ibuprofen and copper and/or zinc such that these components are present in a complex in comparable amounts. One method of determining the content of a complex in a treated cellulosic material is to burn the material and analyze the ash for its content of the components that have been used to prepare the complex. A composition hereof may be made by mixing the components in any suitable device, such as a blender or rotating mixer.

Though the preservative compositions of this invention that are used in treating cellulosic materials are largely if not completely dissolved in solutions such as ammoniacal solutions, a more concentrated master batch may be made that is readily transported for commercial purposes, and then diluted prior to use. Such a concentrated master batch may be a slurry, containing partially precipitated ibuprofen-copper and/or zinc complexes. The slurry is prepared for use in treatment by increasing the volume of solution by the addition of one or more solvents or co-solvents, for example to a final concentration where ammonia is used in the solvent system and an approximately 1.4 wt % ammoniacal water solution is obtained.

Features of Ibuprofen and Copper and/or Zinc Complexes in Ammoniacal Solution as Wood Preservative Compositions The solubility properties of the ibuprofen and copper and/or zinc complexes as used herein provide specific attributes valuable in a preservative composition. These complexes are insoluble in water, but have been found to typically be well dissolved, if not be completely soluble, in a solvent system such as an ammoniacal solution. When the complex is well dissolved in the solvent system, deep penetration of the preservative solution into cellulosic material such as wood, well past the surface wood, is obtained. Following penetration, a solvent or co-solvent such as ammonia readily evaporates from the wood, leaving the brown-rot fungicidal and termiticidal ibuprofen and the white-rot fungicidal copper and/or zinc ions as a complex in the wood where it becomes precipitated and binds tenaciously to cellulose. Thus, there is little leaching of ibuprofen or copper and/or zinc ions from the treated wood.

Additional Components in Wood Preservative Solution

Preservative compositions of this invention may include antifungal and/or termiticidal components in addition to those discussed above, singly or in combinations. Examples include without limitation tungstate and/or molybdate ions as described in U.S. Provisional Application No. 60/755,213; tropolones as described in U.S. Provisional Application No. 60/755,242; and hydrolyzed olefin/maleic anhydride copolymers as described in U.S. Provisional Application No. 60/755,211; each of the above provisional applications being incorporated in its entirety as a part hereof for all purposes.

Molybdate and/or tungstate ions used as additional components in preservative solutions of this invention may be obtained from any soluble source of molybdate or tungstate, such as potassium molybdate, ammonium molybdate, sodium molybdate dihydrate, molybdenum oxide, molybdic acid, potassium tungstate, ammonium tungstate, sodium tungstate dihydrate, tungsten oxide, tungstic acid. Additional compounds that may be used as sources of tungstate or molybdate ions include compounds such as silicotungstates, phosphotungstates, borotungstates, silicomolybdates, phosphomolybdates and boromolybdates.

Molybdate and/or tungstate ions form complexes with copper and/or zinc ions that are insoluble in water, but that have substantial if not complete solubility in a solvent system such as an ammoniacal solution. These components penetrate a cellulosic material such as wood when dissolved in solution, and are retained in the wood after loss of the ammonia. When molybdate and/or tungstate ions are used as additional preservative components in a composition having complexes of copper and/or zinc, copper and/or zinc is added in sufficient amount to form complexes with both the ibuprofen component and the molybdate and/or tungstate component. Suitable amounts of molybdate and/or tungstate ions range from about 10 to about 6,000 ppm depending on factors related to the use to be made of the cellulosic material, as discussed above. Particularly suitable is a concentration between about 200 and about 1,700 ppm.

The term "tropolone" is commonly used to refer to tropolone itself (2-hydroxycyclohepta-2,4,6-trienone) and compounds that are derivatives of tropolone and have similar properties, such as the natural compounds beta-thujaplicin (also known as hinokitiol), gamma-thujaplicin, and beta-dolabrin. Any of these tropolones having antifungal and/or termiticidal activity may be used as additional components in the preservative compositions of this invention. These compounds are soluble in methanol and ethanol but relatively insoluble in water.

Tropolones also form complexes with copper and/or zinc ions that are insoluble in water but that have substantial if not complete solubility in a solvent system such as an ammoniacal solution. This component penetrates a cellulosic material such as wood when dissolved in solution, and is retained in the wood after loss of a solvent such as ammonia. When a tropolone is used as an additional preservative component in a composition containing copper and/or zinc ions, copper and/or zinc is added in an amount sufficient to form a complex with both the ibuprofen component and the tropolone component. Suitable amounts of tropolone for use in a composition hereof range from about 100 to about 1,000 ppm depending on factors related to the use to be made of the cellulosic material, as discussed above. Particularly suitable is a concentration between about 200 and about 700 ppm.

Hydrolyzed olefin/maleic anhydride copolymers form complexes with copper and/or zinc ions that are insoluble in water, but that have substantial if not complete solubility in a solvent system such as an ammoniacal solution. This component penetrates a cellulosic material such as wood when dissolved in solution, and is retained in the wood after loss of a solvent such as ammonia. When hydrolyzed olefin/maleic anhydride copolymers are an additional preservative component in a composition containing copper and/or zinc ions, copper and/or zinc ions are added in an amount sufficient to form a complex with both the ibuprofen component and the hydrolyzed olefin/maleic anhydride copolymer component.

Hydrolyzed olefin/maleic anhydride copolymers are prepared by hydrolysis of olefin/maleic anhydride copolymers, using for example aqueous NaOH, to form negatively charged carboxylate anions which can complex with copper and zinc ions. Olefins of particular use in the olefin/maleic anhydride copolymers for hydrolysis are octene and styrene. Mixtures of different types of olefin/maleic anhydride copolymers, such as a mixture of octene/maleic anhydride copolymer and styrene/maleic anhydride copolymer may also be used. The synthesis of olefin/maleic anhydride copolymers is known from sources such as U.S. Pat. No. 3,706,704 and U.S. Pat. No. 3,404,135, and copolymers suitable for use herein are generally between about 10,000 and about 50,000 in molecular weight.

A preferred process for the synthesis of styrene/maleic anhydride copolymers, which results in copolymers of molecular weight ranging between 20,000 and 100,000, depending on the specific conditions used, makes use of a combination of toluene and isopropyl alcohol as both a solvent and as a chain transfer agent. Using this combination, rather than isopropyl alcohol alone, reduces the percent of mono isopropyl maleate ester formed during the polymerization from about 20% to about 1%. In addition, the molecular weight of the copolymer product is increased from about 18,000 when using isopropyl alcohol alone, to over 20,000 when using a toluene:isopropanol ratio of 1:1. Molecular weights of over 90,000 may be achieved using a ratio of 76:4.

Copolymers of up to about 1,000,000 molecular weight may be used in the preservative compositions of the invention, but, in concentrated solution, copolymers with greater than about 80,000 molecular weight are viscous and therefore difficult to use. Therefore, preferred in this invention are olefin/maleic anhydride copolymers with molecular weight below about 80,000. More preferred are copolymers with molecular weights ranging between 2,000 and about 40,000.

In addition, a copper chelating compound, such as is described in U.S. Pat. No. 6,978,724 (which is incorporated in its entirety as a part hereof for all purposes), may be included in a composition hereof to enhance copper retention in treated articles. A suitable copper chelating compound may have a functional group such as one r more of the following: amidoximes, hydroxamic acids, thiohydroxamic acids, N-hydroxyureas, N-hydroxycarbamates, and N-nitroso-alkyl-hydroxylamines. A suitable copper chelating compound forms a complex with copper and/or zinc that is insoluble in water, but has solubility in an ammoniacal solution that is similar to the solubility of the ibuprofen--copper and/or zinc complex described above. The complex formed by the chelating compound also penetrates a cellulosic material deeply when dissolved in the solution, and is retained in the wood after loss of a solvent or co-solvent such as ammonia. When a copper chelating compound is present as an additional component in a composition of this invention, copper and/or zinc ions are added in sufficient amount such that it/they form complexes with both the ibuprofen and the chelating compound.

A functional group in a copper chelating compound can be provided by methods such as the following: in an amidoxime, reacting nitrile-containing compounds with hydroxylamine; in a hydroxamic acid, adding hydroxylamine to anhydride groups of copolymers such as styrene/maleic anhydride or octene/maleic anhydride, and forming styrene/N-hydroxymaleamic acid copolymer or octene/N-hydroxymaleamic acid copolymer; in a thiohydroxmic acid, adding hydroxylamine to dithiocarboxylic acids; in a N-hydroxyurea, reacting hydroxylamine with an isocyanate; in a N-hydroxycarbamate, by reacting hydroxylamine with either a linear or cyclic carbonate; and in a N-nitroso-alkyl-hydroxylamine, by nitrosation of alkyl hydroxylamines.

Preferred chelating compounds contain two or more amidoxime and/or hydroxamic acid groups. By acid catalysis, the amidoxime functionality can be readily converted to the corresponding hydroxamic acid functionality in aqueous solution. A convenient route to this preferred class of compounds is by addition of hydroxylamine to the corresponding nitrile compound. Various methods are known for preparing nitrile compounds. A particularly useful method is cyanoethylation, in which acrylonitrile, or other unsaturated nitrile, undergoes a conjugate addition reaction with protic nucleophiles such as alcohols and amines. Preferred amines for cyanoethylation are primary amines, secondary amines having 1 to 30 carbon atoms, and polyethylene amine. Preferably, a cyanoethylation catalyst is used, such as lithium hydroxide, sodium hydroxide, or potassium hydroxide, between about 0.05 mol % and 15 mol % based on unsaturated nitrile.

A wide variety of materials can be cyanoethylated. Cyanoethylates can be derived from the reaction of acrylonitrile with carbohydrates, such as regenerated cellulose, dextran, dextrin, gums (guar, locust bean, honey locust, flame tree, tara, arabic, tragacanth, and karaya); starches (corn, potato, tapioca and wheat); or modified natural polymers such as cellulose xanthate, dimethylthiourethane of cellulose, ethyl cellulose, ethylthiourethane of cellulose, hydroxyethylcellulose, methylcellulose, and phenylthiourethane of cellulose. Other natural polymers that have been cyanoethylated include flax, jute, manila, sisal, and proteins such as blood albumin, casein, gelatin, gluten, soybean protein, wool, corn zein, or materials derived from such natural polymers. Pretreatment of high molecular weight or water-insoluble carbohydrates and starches with enzymes may be used if necessary to increase the solubility of the amidoxime or hydroxamic acid copper complex in an aqueous ammonia, ethanolamine or pyridine solution.

Synthetic polymers such as acetone-formaldehyde condensate, acetone-isobutyraldehyde condensate, methyl ethyl ketone-formaldehyde condensate, poly(allyl alcohol), poly(crotyl alcohol), poly(3-chloroallyl alcohol), ethylene-carbon monoxide copolymers, polyketone from propylene, ethylene and carbon monoxide, poly(methallyl alcohol, poly(methyl vinyl ketone, and poly(vinyl alcohol) have also been cyanoethylated and can also serve as platforms for further modification into metal-binding polymers.

Preferably the cyanoethylates are derived from sucrose and sorbitol. Most preferred is cyanoethylated sorbitol (DS=6.0), called CE-Sorb6.

The nitrile groups of these cyanoethylates or cyanoalkylates can be reacted with hydroxylamine to form the amidoxime or hydroxamic acid. If hydroxylamine hydrochloride is used instead of hydroxylamine, sodium hydroxide, sodium carbonate or ammonium hydroxide may be used to neutralize the hydrochloric acid. Ammonium hydroxide is preferred. The amidoxime of sorbitol can be prepared by hydroxylamine reaction of CE-Sorb6. This amidoxime of sorbitol is particularly useful as an additional component in the preservative compositions of this invention.

Preservative Treatment A solution of ibuprofen and copper and/or zinc complexes, optionally containing additional preservative compounds, may be applied by dipping, brushing, spraying, soaking, draw-coating, rolling, pressure-treating or other known methods. The preservative compositions may be applied to any cellulosic material, including for example wood, lumber, plywood, oriented strand board, cellulose, hemicellulose, lignin, cotton and paper. Particularly efficacious is imbibing into wood under the standard pressure treatment process for waterborne preservative systems. A vacuum may be applied before and/or after application of the wood preservative. Removal of air from the wood under vacuum, then breaking the vacuum in the presence of preservative solution, enhances penetration of the solution into the wood.

A particularly useful treatment process for wood is as follows: Wood, either dry or fresh cut and green is placed in a chamber that is then sealed and evacuated in a regulated cycle which is determined by the species of wood. Generally, for Southern Yellow Pine (SYP) wood, the period of evacuation is about 30 minutes, during which time the pressure within the sealed chamber is brought to a level of about two inches of mercury or less. The evacuated pressure in the chamber can vary from 0.01 to 0.5 atm. The purpose of this step is to remove air, water, and volatiles from the wood. The preservative compositions of the invention then are introduced into the closed chamber in an amount sufficient to immerse the wood completely without breaking the vacuum to the air. Pressurization of the vessel is then initiated and the pressure maintained at a desired level by a diaphragm or other pump for a given period of time. Initially, the pressure within the vessel will decrease as the aqueous composition within the container penetrates into the wood. The pressure can be raised to maintain a desirable level throughout the penetration period of treatment. Stabilization of the pressure within the vessel is an indication that there is no further penetration of the liquid into the wood. At this point, the pressure can be released, the wood allowed to equilibrate with the solution at atmospheric pressure, the vessel drained, and the wood removed. In this part of the process, the pressures used can be as high as 300 psig, and are generally from about 50 to 250 psig.

Articles Incorporating Preservative Compositions

Articles of this invention are those having been treated with a preservative composition described herein. Following treatment of articles such as those made from or incorporating wood, lumber, plywood, oriented strand board, paper, cellulose, cotton, lignin, and hemicellulose, the ammonia in an ammoniacal solution of the preservative composition will dissipate. The ibuprofen—copper and/or zinc complex is retained on and/or in the article. Additional components, if included in the composition used for treatment, are retained on and/or in the treated articles as well.

Compositions containing components in addition to an ibuprofen-copper and/or zinc complex that are particularly suitable for treatment of an article include those that contain hydrolyzed olefin/maleic anhydride copolymers; copper chelating compounds having at least two functional groups selected from amidoximes, hydroxamic acids, thiohydroxamic acids, N-hydroxyureas, N-hydroxycarbamates, and N-nitroso-alkyl-hydroxylamines; molybdate and/or tungstate ions; or a tropolone; and mixtures of these components. Particularly useful in such compositions is a copper chelating compound with at least two hydroxamic groups being derived from styrene/maleic anhydride or octene/maleic anhydride, or a copper chelating compound based on an amidoxime of sorbitol.

The process of this invention for treating cellulosic material also includes a step of incorporating the cellulosic material, or a treated article containing the cellulosic material, such as wood, into a structure such as a house, cabin, shed, burial vault or container, or marine facility, or into a consumable device such as a piece of outdoor furniture, or a truss, wall panel, pier, sill, or piece of decking for a building.

EXAMPLES

The present invention is further illustrated in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

The meaning of abbreviations is as follows: "conc." means concentrated, "sec" means second(s), "ml" means milliliter(s), "L" means liter(s), "g" means gram(s), "mmol" means millimole(s), "mtorr" means millitorr(s), "hr" means hour(s), "min" means minute(s), "mm" means millimeter(s), "cm" means centimeter(s), "nm" means nanometer(s), "Mw" means weight average molecular weight, "Mn" means number average molecular weight, "mw" means molecular weight, "XRF" stands for X-ray fluorescence spectroscopy, "RH" is relative humidity, "MHz" means megahertz, "NMR" means nuclear magnetic resonance, "IR" means infrared, "ICP" means ion couples plasma, "LC/MS means liquid chromatography/mass spectroscopy, and "S/S" means stainless steel. "SD" is standard deviation, "SMA" is styrene/maleic anhydride copolymer, "SMA-NOH" is styrene/N-hydroxymaleamic acid copolymer, "OMA" is octene/maleic anhydride copolymer. "SYP" is "southern yellow pine", an acronym for closely related pine species that includes Pinus caribaea Morelet, Pinus elliottii Englelm., Pinus palustris P. Mill., Pinus rigida P. Mill., and Pinus taeda L. "AWPA" is the American Wood-Preserver's Association. AWPA standards are published in the "AWPA Book of Standards", AWPA P.O. Box 5690, Granbury, Tex. 76049. The protocol for preservation of SYP stakes is based on AWPA Standard, Method E7-01, Sec. 4, 5, 6, and 7 and E11-97. According to AWPA Standard E7-01, the stakes are graded visually according to the following criterion for fungal decay and insect attack as follows:

| Decay Grades | |
|---|---|
| Grade No. | Description of Condition |
| 10 | Sound. |
| 9.5 | Suspicion of decay permitted |
| 9 | Trace decay to 3% of cross section |
| 8 | Decay from 3 to 10% of cross section |
| 7 | Decay from 10 to 30% of cross section |
| 6 | Decay from 30 to 50% of cross section |
| 4 | Decay from 50 to 75% of cross section |
| 0 | Failure |

| Termite Grades | |
|---|---|
| Grade No. | Description of Condition |
| 10 | Sound. |
| 9.5 | 1 to 2 small nibbles permitted |
| 9 | Slight evidence of feeding to 3% of cross section |
| 8 | Attack from 3 to 10% of cross section |
| 7 | Attack from 10 to 30% of cross section |
| 6 | Attack from 30 to 50% of cross section |
| 4 | Attack from 50 to 75% of cross section |
| 0 | Failure |

The termite grades and decay grades are used to report insect damage and wood decay, respectively, in the tables below. "Gross retention" refers to the amount of treatment liquid remaining in the wood immediately after imbibition. "Retention" refers to the amount of preservative remaining in the wood after the imbibing liquid has been removed from the wood by drying. The amount can be expressed as ppm or as a weight. A "witness stake" or "witness sample" is a whole stake, or a portion of a treated stake, that will be retained as a sample for future analysis. "DS" is degree of substitution.

General Methods

All reactions and manipulations were carried out in a standard laboratory fume hood open to atmosphere. Deionized water was used where water is called for in the subsequent procedures. Sorbitol, AIBN, acrylonitrile, lithium hydroxide monohydrate, hydroxylamine hydrochloride, copper sulfate pentahydrate, and Chromazurol S [1667-99-8] were obtained from Sigma-Aldrich Chemical (Milwaukee, Wis.) and used as received. Concentrated ammonium hydroxide and glacial acetic acid were obtained from EM Science (Gibbstown, N.J.) and used as received. Cyanoethylated sucrose [18307-13-7] and copper acetate monohydrate were obtained from Acros Organics (Geel, Belgium) and used as received. Sucrose was obtained from Pathmark Supermarket (Wilmington, Del.) and used as received. pH was determined with pHydrion paper from Micro Essential Laboratory (Brooklyn, N.Y.). Degree of substitution (DS) of the cyanoethylate is expressed in terms of equivalents of acrylonitrile used in the cyanoethylation step. IR spectra were recorded using a Nicolet Magna 460 spectrometer. LC/MS analyses were performed using a Micromass LCT instrument. NMR spectra were obtained on a Bruker DRX Avance (500 MHz $^{1}$H, 125 MHz $^{13}$C) using deuterated solvents obtained from Cambridge Isotope Laboratories. Elemental analyses were performed by Micro-Analytical Inc, Wilmington, Del. Pressure treatment of southern yellow pine wood was performed in a high-pressure lab using stainless steel pressure vessels following the AWPA standard process (AWPA P5-01). XRF analysis was performed on an Axios Wavelength Dispersive X-ray Fluorescence Spectrometer manufactured by Panalytical Inc., Eindhoven, Netherlands.

Chromazurol S Test for Presence of Copper

Treated wood was tested for the presence of copper with Chromazurol S using the method described by AWPA A3-00 Sec. 2. A 0.167% w/w Chromazurol S in 1.67% w/w aqueous sodium acetate solution was sprayed onto a freshly cut treated wood surface. A change from the yellow solution color to a dark blue color in the sprayed area indicates that a minimum of 25 ppm copper is present. Stakes 965 mm (38") long are cut to 457 mm (18") from each end and the remaining 50.8 mm (2") piece (witness piece) in the middle was treated on the freshly cut surface with the spray solution of Chromazurol-S. A freshly cut surface turned dark blue on exposure to the solution, which is an indication of complete penetration of the wood by the wood preservative treatment solution.

Dimensions of Wood as per AWPA E17-01 Sec. 4.2.4:

All wood was cut using inch measurements. The wood was cut as accurately as practicable, given that wood will change dimensions with moisture content; the cutting error is estimated to be within one mm in any dimension. Conversions to metric are provided.

Fahlstrom stake: 0.156"×1.5"×10" (4 mm×38 mm×254 mm)
Decay stake: ¾"×¾"×18" (19 mm×19 mm×450 mm)
Pre-Decay stakes: ¾"×¾"×38" (19 mm×19 mm×1154 mm)
Depletion stake: 1.5"×1.5"×18" (38 mm×38 mm×450 mm)
Blocks: ¾"×¾"×¾" (19 mm×19 mm×19 mm)

Preparation of Styrene/Maleic Anhydride Copolymer

Styrene/maleic anhydride copolymer (SMA) was prepared as described in co-pending application with US filing #60/855211, which is herein incorporated by reference, as follows.

An 18 L multi-necked flask was equipped with two dropping funnels, reflux condenser, heating mantel, mechanical stirrer, and nitrogen bubbler. The flask was charged with 9500 g (11 L) of toluene and 500 g (640 ml) of isopropanol. To this solution was added 1276 g of maleic anhydride powder. A solution of 15 g of AIBN dissolved in 500 g (578 ml) of toluene was prepared and placed in one of the dropping funnels. The second funnel was charged with 1302.6 g of styrene. The apparatus was sealed and purged with nitrogen. The maleic anhydride solution was warmed to 60° C. and about one-third of the AIBN solution was added. Then about 150 ml of styrene was added to the flask from the funnel. There was about a 5 minute induction period during which oxygen was consumed. After a white precipitate began to form, indicating that the polymerization had begun, the remaining styrene was added in 150 ml portions during 60 minutes. The AIBN solution was added in thirds over 60 minutes. The addition of styrene and AIBN maintained the reaction temperature at about 70° C. to 80° C. without much additional heat from the mantel. After addition was complete, the reaction temperature was maintained at about 80° C. for an additional 2 hours by using the heating mantel. The white slurry of copolymer was then cooled to about room temperature, filtered, washed with warm toluene, and dried in a vacuum oven at 90° C. to obtain 2460 g (95.5% yield) of SMA and 40 g of mono isopropyl maleate. The Mw =40,400 and the Mn=18,600. The washings were evaporated to give an additional 0.4 g of mono isopropyl maleate ($^1$H NMR (CDCl$_3$): δ1.32 (d, J =1.2, CH3, 6H) , 5.15 (m, CH, 1H), 6.36 (m, CH, 2H) ppm.

Preparation of Hydrolyzed Octene/Maleic Anhydride Copolymer

A 1:1 co-polymer of octene and maleic anhydride monosodium salt was prepared as described in U.S. Pat. Nos. 3706704 and 3404135. The Mw of the octane/maleic anhydride copolymer (OMA), which is the precursor of hydrolyzed 1:1 octene/maleic anhydride copolymer monosodium salt, was determined by size exclusion chromatography to be 8595+/−50. The resulting co-polymer was hydrolyzed with aqueous sodium hydroxide solution and brought to a 27.1% w/w solution in water.

Preparation of CE-Sorb6: Cyanoethylation of Sorbitol

A 1000 ml 3-necked round-bottomed flask equipped with an mechanical stirrer, reflux condenser, nitrogen purge, dropping funnel, and thermometer was charged with water (18.5 ml) and lithium hydroxide monohydrate (1.75 g) and the first portion of sorbitol (44.8 g). The solution was heated to 42° C. with a water bath with stirring and the second portion of sorbitol (39.2 g) was added directly to the reaction flask. The first portion of acrylonitrile (100 ml) was then added to the reaction drop-wise via a 500 ml addition funnel over a period of 2 hr. The reaction was slightly exothermic, raising the temperature to 51° C. The final portion of sorbitol (32 g) was added for a total of 0.638 moles followed by a final portion of acrylonitrile (190 ml) over 2.5 hr while keeping the reaction temperature below 60° C. (A total of 4.41 moles of acrylonitrile was used.) The reaction solution was then heated to 50-55° C. for 4 hr. The solution was then allowed to cool to room temperature and the reaction was neutralized by addition of acetic acid (2.5 ml). Removal of the solvent under reduced pressure gave the product as a clear, viscous oil (324 g). The IR spectrum showed a peak at 2251 cm$^{-1}$, indicative of the nitrile group. A DS=5.6 was determined by LC/MS, which is rounded to 6 in CE-Sorb6.

Reaction of CE-Sorb6 with Hydroxylamine Hydrochloride

A 1000 ml three-necked round-bottomed flask was equipped with a mechanical stirrer, condenser, and addition funnel under nitrogen. CE-Sorb6 (14.77 g, 29.5 mmol) and water (200 ml) were added to the flask and stirred. In a separate 500 mL Erlenmeyer flask, hydroxylamine hydrochloride (11.47 g, 165 mmol, 5.6 eq) was dissolved in water (178 ml) and then treated with ammonium hydroxide (22.1 ml of 28% ammonia solution, 177 mmol, 6.0 eq) for a total volume of 200 ml. The hydroxylamine solution was then added in one portion directly to the mixture in the round-bottomed flask at room temperature. The stirred mixture was heated at 80° C. for 2 hr, pH=8-9, and then allowed to cool to room temperature. The IR spectrum indicated loss of most of the nitrile peak at 2250 cm$^{-1}$ and the appearance of a new peak at 1660 cm$^{-1}$, indicative of the amidoxime or hydroxamic acid.

EXAMPLE 1

Ammoniacal Solution of Styrene/N-Hydroxymaleamic Acid Copolymer, Ibuprofen/Copper Complex, and Molybdate/Copper Complex as Preservative A) Preparation of Styrene/N-Hydroxymaleamic Acid Copolymer, Ibuprofen/Copper Complex, and Molybdate/Copper Complex in Ammoniacal Solution A 5 L round-bottomed flask equipped with addition funnel, heating mantel, thermocouple well, and mechanical stirrer was charged with 72.2 g (0.357 mol) of styrene/maleic anhydride copolymer (SMA) resin (prepared as described in General Methods) and 500 ml of water. A solution of 23.6 g of hydroxylamine 50% w/w in water (0.357 mol) and 18.9 g sodium carbonate (0.179 mol) in 101 ml of water was added through the addition funnel during 15 minutes. The mixture was heated for 3 hours at 55° C. to give a clear solution containing styrene/N-hydroxymaleamic acid copolymer. To the polymer solution was added 250 g of conc. ammonium hydroxide, 250 ml of water, 11.1 of sodium ibuprofen (Aldrich, Milwaukee, Wis.), 15.14 g of sodium molybdate dihydrate, and 116.7 g (0.468 mol) of copper sulfate pentahydrate. The product was diluted with water to a final weight of 20 Kg to give an imbibing solution containing 1485 ppm copper, 500 ppm of ibuprofen, and 500 ppm of molybdate ion.

B) Wood preservation treatment procedure and Environmental Testing for Decay Stakes Treated with Ammoniacal Solution of Ibuprofen/Copper Complex, Molybdate/Copper Complex, and Styrene/N-Hydroxymaleamic Acid Copolymer Selection and Preparation of Stakes The following methods are based on AWPA Standard, Method E7-01, Sec. 4, 5, 6, and 7 and E11-97.

SYP boards, 3.175 cm×35.56 cm×243.84 cm (⅝"×14"×8 ft) and 3.175 cm×30.48 cm×243.84 cm (⅝"×12"×8 ft) were obtained from Delaware County Supply (Boothwin, Pa.). The boards were cut into pre-decay stakes of 19 mm×19 mm×96.5 cm (¾"×¾"×38") in size (AWPA Standard, Method E7-01, Sec 4.2, with the exception that the boards were milled without equilibration). The stakes were segregated by visual inspection (AWPA Standard, Method E7-01, Sec. 4.1) and stakes having knots, cracks, resin and sap pockets, signs of infection by mold, stain, and wood destroying fungi were eliminated. The remaining stakes were sorted into groups by weight (AWPA Standard, Method E7-01, Sec. 5). The group of stakes weighing between 200 g and 220 g was chosen for the imbibing experiment and placed in a controlled environment chamber at 23° C. and RH of 50% (Model 1-60LLVL Humidity Cabinet, Percival Scientific Inc., Boone, Iowa) for 21 days (AWPA Standard, Method E7-01, Sec. 4 and E11-97, Sec. 3). After equilibration in the environment chamber, each stake was equipped with two S/S identification tags and secured with 24.6 mm S/S nails. Each stake was then weighed (weights given in Table 1: Dry weight) and dimensioned and the results recorded.

Wood Preservation Treatment Procedure

Treatment was carried out in a stainless steel pressure vessel designed and fabricated at the DuPont Experimental Station (Wilmington, Del.). Pressure was supplied by a Diaphragm Pump (Model S216J10; Sprague Products Div. of Curtiss-Wright Flow Control Corp., Brecksville, Ohio). The pressure vessel was constructed from sched. 80 SS pipe measuring 12.7 cm (5") diam. and was closed at each end with SS flanges and caps. The length of the pipe varied depending on the length of the wood to be treated. Typically, a 101.6 cm (40") length was chosen for treating 38" wood specimens. Other lengths of pipe were added via flanges to extend the length of the pressure vessel to accommodate 243.84 cm (8 ft) specimens or shorter lengths of pipe were used to treat 25.4 cm (10") specimens.

Ten labeled pre-decay stakes were loaded into a stainless steel separation rack (to simulate sticking, which is physical separation of lumber by placing small pieces of wood between boards to separate them), as well as two witness stakes (total 12 stakes), and placed in the pressure vessel. The pressure vessel was sealed and a vacuum of 69.85 cm Hg gauge (13.5 psig) was applied for a period of 30 minutes. The vacuum was broken by introduction of the imbibing fluid (the solution prepared in Example 1A) to fill the pressure vessel and cover the wood. Air pockets were removed by circulating imbibing fluid through the vessel, and pressure of 7.18 kilopascal gauge (150 psig) was applied with a diaphragm pump for a period of 30 minutes. The pressure was released and the stakes allowed to equilibrate in the imbibing solution for 15 minutes. The pressure vessel was drained and the treatment rack bearing the stakes was removed. The stakes were lightly wiped with a paper towel, weighed (weights given in Table 1: Wet weight), and placed on open racks in a ventilated enclosure to dry. The original dry weight subtracted from the wet weight for each block indicated the amount of uptake of treatment solution, as given in Table 1.

TABLE 1

Penetration of Treatment Solution in SYP Pre-Decay Stakes

| Stake ID | Dry wt (g) | Wet wt (g) | Gross retention (g) | Dry Wt. 3 wks (g) |
|---|---|---|---|---|
| F1767 | 211.06 | 458.16 | 247.1 | 212.37 |
| F1769 | 209.26 | 466.97 | 257.71 | 210.6 |
| F1771 | 203.37 | 454.77 | 251.4 | 205.59 |
| F1773 | 193.25 | 431.84 | 238.59 | 194.5 |
| F1775 | 206.12 | 452.81 | 246.69 | 207.33 |
| F1777 | 207.03 | 455.74 | 248.71 | 209.87 |
| F1779 | 203.81 | 442.08 | 238.27 | 204.9 |
| F1781 | 192.99 | 450.63 | 257.64 | 194.78 |
| F1783 | 202.01 | 454.16 | 252.15 | 203.31 |
| F1785 | 207.96 | 454.46 | 246.5 | 209.78 |

After 14 days the stakes were weighed, the results recorded, and returned to the humidity chamber. After a total of 21 days in the chamber, the stakes were weighed and the results recorded in Table 1 column 5 (AWPA Standard, Method E7-01, Sec. 6).

Two additional sets of stakes, prepared as described above, were separately imbibed with 1:2 and 1:4 dilutions of the solution prepared in Example 1A. Dilutions were made with a 1.4% ammonia water solution. In addition, a set of stakes was prepared and imbibed with a 1.4% ammonia water solution to serve as controls.

The four sets of 10 labeled stakes were cut to 45.7 cm (18") decay stake length, cutting from each end and leaving a 5.1 cm (2") witness section from the center of the stake. All witness sections were tested for copper penetration using the Chromazurol S test described in the General Methods. All witness sections tested turned dark blue indicating complete penetration of the wood by the wood preservative treatment solution.

Each 45.7 cm (18") stake was weighed, dimensioned and the results recorded. The groups of 10 stakes from each half were bundled together and labeled for ground insertion at two separate test sites (Newark, Del. and Starke, Fla.). The bundles were stored in a cool area (AWPA Standard, Method E7-01, Sec. 7) until the stakes were installed in the ground. The stakes were placed in the ground as per AWPA E7-01. The positioning of the stakes was randomized in the test sites as per AWPA E7-01. At 12 months the stakes in Starke, Fla. were removed from the ground and visually graded for decay and termite attack (insect damage) according to AWPA protocol E7-01. Results are given in Table 2, along with the average of gradings for a set of stakes with the same treatment solution, and the standard deviation. A score of 10 indicates no decay or damage. A score of 0 indicates complete decomposition.

TABLE 2

Decay and insect damage data for stakes treated with different dilutions of styrene/N-hydroxymaleamic acid copolymer, ibuprofen/copper complex, and molybdate/copper complex and tested in Starke, FL.

| Treatment | Stake ID | 12 mo grading Decay | Insect damage |
|---|---|---|---|
| 00189 | F1768 | 10 | 10 |
| 1485 ppm Cu/500 ppm MoO$_4$/ | F1770 | 10 | 10 |
| 500 ppm Ibuprofen/SMA-NOH | F1772 | 10 | 10 |
|  | F1774 | 10 | 10 |
|  | F1776 | 10 | 10 |
|  | F1778 | 9 | 8 |
|  | F1780 | MD | MD |
|  | F1782 | 10 | 10 |
|  | F1784 | 10 | 10 |
|  | F1786 | 10 | 10 |
|  | Avg | 9.9 | 9.8 |
|  | SD | 0.31 | 0.63 |
| 00190 | F1838 | 10 | 10 |
| 743 ppm Cu/250 ppm MoO$_4$/250 ppm | F1840 | 9 | 10 |
| Ibuprofen/SMA-NOH | F1842 | 8 | 10 |
|  | F1844 | 10 | 10 |
|  | F1846 | 10 | 10 |
|  | F1848 | 10 | 10 |
|  | F1850 | 10 | 10 |
|  | F1852 | 9 | 10 |
|  | F1854 | 7 | 10 |
|  | F1856 | 10 | 10 |
|  | Avg | 9.3 | 10 |
|  | SD | 1.01 | 0 |
| 00191 | F1858 | 10 | 10 |
| 371 ppm Cu/125 ppm MoO$_4$/125 ppm | F1860 | 10 | 10 |
| Ibuprofen/ | F1862 | 8 | 8 |
| SMA-NOH | F1864 | 10 | 10 |
|  | F1866 | 10 | 9 |
|  | F1868 | 9 | 8 |
|  | F1870 | 10 | 10 |
|  | F1872 | 10 | 10 |
|  | F1874 | 7 | 7 |
|  | F1876 | 7 | 8 |
|  | Avg | 9.1 | 9 |
|  | SD | 1.22 | 1.10 |
| 00195 | F1988 | 10 | 10 |
| Solvent Control Water/Ammonia | F1990 | 7 | 7 |
|  | F1992 | 8 | 10 |
|  | F1994 | 9 | 10 |
|  | F1996 | 9 | 10 |
|  | F1998 | 10 | 10 |
|  | F2000 | 9 | 10 |
|  | W0402 | 10 | 10 |
|  | W0404 | 10 | 10 |
|  | W0406 | 10 | 9 |
|  | Avg | 9.2 | 9.6 |
|  | SD | 0.98 | 0.92 |

MD = mechanical damage

At 12 months the stakes in Newark, Del. were removed from the ground and graded. A summary of the results are given in Table 3 as averages of the gradings, along with averages of the gradings at Starke from Table 2.

TABLE 3

Averages of decay and insect damage scores for stakes treated with different dilutions of styrene/N-hydroxymaleamic acid copolymer, ibuprofen/copper complex, and molybdate/copper complex and tested in Newark, DE and Starke, FL.

| Location | Treatment | Time (Months) | Avg Decay | Avg insect damage |
|---|---|---|---|---|
| Starke, FL | 1485 ppm Cu/500 ppm MoO$_4$/500 ppm Ibupofen/SMA-NOH | 12 | 9.9 | 9.8 |
|  | 743 ppm Cu/250 ppm MoO$_4$/250 ppm Ibupofen/SMA-NOH | 12 | 9.3 | 10 |
|  | 371 ppm Cu/125 ppm MoO$_4$/125 ppm Ibupofen/SMA-NOH | 12 | 9.1 | 9 |
|  | Control | 12 | 9.2 | 9.6 |
| Newark, DE | 1485 ppm Cu/500 ppm MoO$_4$/500 ppm Ibupofen/SMA-NOH | 12 | 10 | 10 |
|  | 743 ppm Cu/250 ppm MoO$_4$/250 ppm Ibupofen/SMA-NOH | 12 | 10 | 10 |
|  | 371 ppm Cu/125 ppm MoO$_4$/125 ppm Ibupofen/SMA-NOH | 12 | 10 | 10 |
|  | Control | 12 | 9.7 | 10 |

Since there was little decay and insect damage at these sites in 12 months, the differences between the treated and control stakes are small to none. It is expected that over longer periods of time, treated stakes will show less decay and insect damage with respect to controls at these sites.

EXAMPLE 2

Ammoniacal solution of Ibuprofen, Styrene/N-Hydroxymaleamic Acid Copolymer and Copper/Tungstate Complex as Preservative A) Preparation of Ibuprofen, Styrene/N-Hydroxymaleamic Acid Copolymer and Copper/Tungstate Complex in Ammoniacal solution A 5 L round-bottomed flask equipped with addition funnel, heating mantel, thermocouple well, and mechanical stirrer was charged with 81.7 g (0.404 mol) of SMA resin (prepared as described in General Methods) and 500 ml of water. A solution of 26.7 g of hydroxylamine 50% w/w in water (0.404 mol) and 21.4 g sodium carbonate (0.202 mol) in 102 ml of water was added through the addition funnel during 15 minutes. The mixture was heated for 3 hours at 55° C. to give a clear solution. To the polymer solution was added 200 g of conc. ammonium hydroxide, 100 ml of water, 11.1 of sodium ibuprofen, 13.3 g of sodium tungstate dihydrate, and 116.7 g (0.468 mol) of copper sulfate pentahydrate. The product was diluted with water to a final weight of 20 Kg to give an imbibing solution containing 1485 ppm copper, 500 ppm of ibuprofen, and 500 ppm of tungstate ion.

B) Penetration of Ammoniacal Solution of Ibuprofen, Styrene/N-Hydroxymaleamic Acid Copolymer and Copper/Tungstate Complex in Wood Blocks The ammoniacal solution of ibuprofen, styrene/N-hydroxymaleamic acid copolymer and copper/tungstate complex prepared in Example 2A was imbibed into wood using a wood impregnation system similar to that described by the American Wood Preservers Association (AWPA) as AWPA Standard, Method E11-97. Standard laboratory glassware and a vacuum pump were used to imbibe 32 pre-weighed Southern Yellow Pine (SYP) wood blocks measuring 19 mm×19 mm×19 mm. The blocks were free of knots, resin and sap pockets, had no visible sign of infection by mold, stain, and wood destroying fungi, had no cracks, had a ring count of 6-10 rings per inch, and contained at least 50% summer wood. The blocks were pre-conditioned for 21 days in a humidity chamber set at 23° C.+/−0.50° C. and relative humidity of 50%+/−2%. Under these conditions the blocks achieved equilibrium moisture content of 9-10%, which was determined by using a Moisture Meter, Model PM6304 from the Control Company (Friendswood, Tex.). The blocks were weighed, and weights recorded in Table 2 (dry weight). An imbibing vessel was prepared using a glass flask measuring 10.16 cm in diam.×30.48 cm long having three openings, two of which were standard taper ground glass 29/26 joints and a central one having a standard taper ground glass 102/75 ball joint. An addition funnel was placed on one of the 29/26 joints and filled with the treatment solution. The wood cubes were placed in the imbibing vessel in a Nylon bag that was weighted with stainless steel nuts to prevent floating and the imbibing vessel was evacuated for 30 min. The vacuum was broken by introduction of 800 ml of imbibing solution. This amount of solution was sufficient to cover the blocks. Thirty-two blocks were imbibed with the ibuprofen, styrene/N-hydroxymaleamic acid copolymer and copper/tungstate_complex ammoniacal solution prepared in Example 2A. The blocks were imbibed under atmospheric pressure for 30 minutes. The blocks were gently wiped with a towel to remove any surface solution and were then immediately weighed while wet to ensure that the wood was penetrated by the imbibing solution. Table 4 shows that the blocks gained weight and that the imbibing was successful.

TABLE 4

Solution Penetration in wood blocks treated with ammoniacal solution of ibuprofen, styrene/N-hydroxymaleamic acid copolymer and copper/tungstate complex.

| ID# | dry wt (g) | wet wt (g) | Gross Retention (g) | |
|---|---|---|---|---|
| E2000111.00164B1 | 3.7651 | 8.7851 | 5.0200 | |
| E2000111.00164B2 | 3.7762 | 8.8288 | 5.0526 | |
| E2000111.00164B3 | 3.7989 | 8.8683 | 5.0694 | |
| E2000111.00164B4 | 3.7024 | 8.9358 | 5.2334 | |
| E2000111.00164B5 | 3.7495 | 8.7519 | 5.0024 | |
| E2000111.00164B6 | 3.7336 | 8.8576 | 5.1240 | * |
| E2000111.00164B7 | 3.7509 | 8.882 | 5.1311 | |
| E2000111.00164B8 | 3.7654 | 8.7191 | 4.9537 | |
| E2000111.00164B9 | 3.6952 | 8.8941 | 5.1989 | * |
| E2000111.00164B10 | 3.7696 | 8.8722 | 5.1026 | |
| E2000111.00164B11 | 3.7383 | 8.8606 | 5.1223 | * |
| E2000111.00164B12 | 3.7243 | 8.8693 | 5.1450 | * |
| E2000111.00164B13 | 3.6304 | 8.4484 | 4.8180 | |
| E2000111.00164B14 | 3.6986 | 8.6108 | 4.9122 | |
| E2000111.00164B15 | 3.7361 | 7.3361 | 3.6000 | |
| E2000111.00164B16 | 3.7174 | 8.8297 | 5.1123 | * |
| E2000111.00164B17 | 3.7336 | 8.7432 | 5.0096 | |
| E2000111.00164B18 | 3.7096 | 8.8448 | 5.1352 | |
| E2000111.00164B19 | 3.7725 | 8.9467 | 5.1742 | |
| E2000111.00164B20 | 3.7318 | 8.7683 | 5.0365 | |
| E2000111.00164B21 | 3.7797 | 8.9181 | 5.1384 | |
| E2000111.00164B22 | 3.6461 | 8.8339 | 5.1878 | |
| E2000111.00164B23 | 3.6815 | 8.8583 | 5.1768 | |
| E2000111.00164B24 | 3.6839 | 8.7593 | 5.0754 | |
| E2000111.00164B25 | 3.7436 | 8.7211 | 4.9775 | |
| E2000111.00164B26 | 3.6802 | 8.8776 | 5.1974 | |
| E2000111.00164B27 | 3.7695 | 8.7463 | 4.9768 | |
| E2000111.00164B28 | 3.6679 | 8.9446 | 5.2767 | |
| E2000111.00164B29 | 3.6875 | 8.8085 | 5.1210 | |
| E2000111.00164B30 | 3.7189 | 8.9465 | 5.2276 | * |
| E2000111.00164B31 | 3.6554 | 8.5079 | 4.8525 | |
| E2000111.00164B32 | 3.6937 | 8.8544 | 5.1607 | |
| | 119.107 | | 161.3220 | |

*marks blocks having a gross retention falling within +/− 5% of the group average Decay stakes were prepared as per Example 1 using the solution prepared in Example 2A. In addition, a 1:2 dilution of the solution prepared in Example 2A, and a 1:4 dilution of the solution prepared in Example 2A were used to treat decay stakes in the same manner. The same control stakes as in Example 1, Table 2 were used for comparison. The stakes were placed in the ground in Starke, Fla. and examined after 12 months for decay and insect damage as per AWPA standard E7-01. The results are given in Table 5.

TABLE 5

Decay and insect damage data for stakes treated with different dilutions of ammoniacal solution of ibuprofen, styrene/N-hydroxymaleamic acid copolymer and copper/tungstate complex and tested in Starke, FL.

| Treatment | Stake ID | 12 mo grading | |
|---|---|---|---|
| | | decay | Insect damage |
| 1485 ppm Cu/500 ppm WO$_4$/500 ppm Ibuprofen/SMA-NOH | F1546 | 10 | 10 |
| | F1548 | 8 | 10 |
| | F1550 | 10 | 10 |
| | F1552 | 10 | 10 |
| | F1554 | 10 | 10 |
| | F1556 | 10 | 10 |
| | F1558 | 10 | 10 |
| | F1562 | 10 | 10 |
| | F1564 | 7 | 7 |
| | F1566 | 10 | 10 |
| | Avg | 9.50 | 9.70 |
| | SD | 1.03 | 0.90 |
| 743 ppm Cu/250 ppm WO$_4$/250 ppm Ibuprofen/SMA-NOH | F1618 | 10 | 10 |
| | F1620 | 10 | 10 |
| | F1622 | 10 | 10 |
| | F1624 | 10 | 10 |
| | F1626 | 7 | 7 |
| | F1628 | 10 | 10 |
| | F1630 | 10 | 10 |
| | F1632 | 10 | 10 |
| | F1634 | 10 | 10 |
| | F1636 | 10 | 10 |
| | Avg | 9.70 | 9.70 |
| | SD | 0.90 | 0.90 |

TABLE 5-continued

Decay and insect damage data for stakes treated with different dilutions of ammoniacal solution of ibuprofen, styrene/N-hydroxymaleamic acid copolymer and copper/tungstate complex and tested in Starke, FL.

| Treatment | Stake ID | 12 mo grading | |
|---|---|---|---|
| | | decay | Insect damage |
| 321 ppm Cu/125 ppm WO$_4$/125 ppm Ibuprofen/SMA-NOH | F1638 | 10 | 10 |
| | F1640 | 10 | 10 |
| | F1642 | 10 | 10 |
| | F1644 | 10 | 10 |
| | F1646 | 6 | 6 |
| | F1648 | 10 | 10 |
| | F1650 | 10 | 10 |
| | F1652 | 10 | 10 |
| | F1654 | 9 | 10 |
| | F1656 | 9 | 8 |
| | Avg | 9.40 | 9.40 |
| | SD | 1.20 | 1.28 |
| 00195 Solvent Control Water/Ammonia | F1988 | 10 | 10 |
| | F1990 | 7 | 7 |
| | F1992 | 8 | 10 |
| | F1994 | 9 | 10 |
| | F1996 | 9 | 10 |
| | F1998 | 10 | 10 |
| | F2000 | 9 | 10 |
| | W0402 | 10 | 10 |
| | W0404 | 10 | 10 |
| | W0406 | 10 | 9 |
| | Avg | 9.20 | 9.6 |
| | SD | 0.98 | .92 |

In a similar manner, Decay Stakes were prepared with the same treatment and environmentally tested in Newark, Del. A summary of the results are given in Table 6 as averages of gradings at Newark, and Starke (from Table 5).

TABLE 6

Averages of decay and insect damage data for stakes treated with different dilutions of ammoniacal solution of ibuprofen, styrene/N-hydroxymaleamic acid copolymer and copper/tungstate complex and tested in Newark, DE, compared to Starke, FL results.

| Location | Treatments: Conc. in ppm | Time (Months) | Avg Decay | Avg Insect damage |
|---|---|---|---|---|
| Starke, FL | Cu 1485/WO$_4$ 500/Ibupofen 500/SMA-NOH | 12 | 9.5 | 9.7 |
| | Cu 743/WO$_4$ 250/Ibupofen 250/SMA-NOH | 12 | 9.7 | 9.7 |
| | Cu 371/WO$_4$ 125/Ibupofen 125/SMA-NOH | 12 | 9.4 | 9.4 |
| | Control | 12 | 9.2 | 9.6 |
| Newark, DE | Cu 1485/WO$_4$ 500/Ibupofen 500/SMA-NOH | 12 | 10 | 10 |
| | Cu 743/WO$_4$ 250/Ibupofen 250/SMA-NOH | 12 | 10 | 10 |
| | Cu 371/WO$_4$ 125/Ibupofen 125/SMA-NOH | 12 | 10 | 10 |
| | Control | 12 | 9.7 | 10 |

Since there was little decay and insect damage at these sites in 12 months, the differences between the treated and control stakes is small to none. It is expected that over longer periods of time, treated stakes will show less decay and insect damage with respect to controls at these sites.

EXAMPLE 3

Ammoniacal Solution of Ibuprofen, Hydrolyzed Octene/Maleic Anhydride Copolymer and Copper/Tungstate Complex as Preservative A) Preparation of Ibuprofen, Hydrolyzed Octene/Maleic Anhydride Copolymer and Copper/Tungstate Complex in Ammoniacal Solution A 2 L resin kettle was charged with 6.64 of sodium ibuprofen, 8.00 g of sodium tungstate dihydrate, 300 g of water and 250 g of conc. ammonium hydroxide. To this solution was added 116.7 g of copper sulfate pentahydrate. To this was added 382.5 g of a 27.1% aqueous solution of hydrolyzed copolymer of octene/maleic anhydride monosodium salt, prepared as described in General Methods. The mixture was diluted with 1.4% ammonium hydroxide to give a final weight of 20 Kg. The final solution contained 1485 ppm of copper, 300 ppm of tungstate ion, and 300 ppm of ibuprofen.

B) Wood Preservation Treatment Procedure and Environmental Testing for Pre-Decay Stakes Treated with Ammoniacal Solution of Ibuprofen, Hydrolyzed Octene/Maleic Anhydride Copolymer and Copper/Tungstate Complex Ten pre-decay stakes were prepared and treated with the solution prepared in Example 3A as described in Example 1B. The uptake (Gross Retention) of treatment solution is evident from the results given in Table 7.

TABLE 7

Retention of Treatment Solution in SYP Pre-Decay Stakes

| ID | Dry Wt (g) | Wet Wt (g) | Gross Retention (g) |
|---|---|---|---|
| W1167 | 216.84 | 463.07 | 246.23 |
| W1169 | 230.06 | 446.52 | 216.46 |
| W1171 | 218.87 | 455.22 | 236.35 |
| W1173 | 216.94 | 455.33 | 238.39 |
| W1175 | 215.46 | 450.57 | 235.11 |
| W1177 | 227.32 | 466.27 | 238.95 |
| W1179 | 214.75 | 448.95 | 234.2 |
| W1181 | 216.68 | 463.57 | 246.89 |
| W1183 | 212.97 | 452.77 | 239.8 |
| W1185 | 219.58 | 447.6 | 228.02 |

The 10 labeled stakes were cut to 45.7 cm (18") lengths, cutting from each end and leaving a 5.1 cm (2") witness section from the center of the stake. All witness sections were tested for copper penetration using the Chromazurol S test described in the General Methods. All witness sections tested turned dark blue indicating complete penetration of the wood by the wood preservative treatment solution.

Each 45.7 cm (18") stake was weighed, dimensioned and the results recorded. The group of 10 stakes from each half were bundled together and labeled for ground insertion at two separate test sites (Newark, Del. and Starke, Fla.). The bundles were stored in a cool area (AWPA Standard, Method E7-01, Sec. 7) until the stakes were installed in the ground. The stakes were placed in the ground as per AWPA E7-01. The positioning of the stakes was randomized in the test sites as per AWPA E7-01. After 12 months the stakes in Starke, Fla. were removed from the ground and visually graded for decay and termite attack (insect damage) according to AWPA protocol E7-01. The results are given in Table 8.

TABLE 8

Decay and insect damage data for stakes treated with ammoniacal solution of ibuprofen, hydrolyzed octene/maleic anhydride copolymer and copper/tungstate complex and tested in Starke, FL.

| | | 12 mo grading | |
|---|---|---|---|
| Treatment | stake ID | decay | Insect damage |
| 1485 ppm Copper/300 ppm WO$_4$/300 ppm Ibuprofen/ hydrolyed OMA | 1168 | 10 | 10 |
| | 1170 | 10 | 10 |
| | 1172 | 10 | 10 |
| | 1174 | 10 | 9 |
| | 1176 | 10 | 10 |
| | 1178 | 10 | 10 |
| | 1180 | 10 | 10 |
| | 1182 | 10 | 10 |
| | 1184 | 10 | 10 |
| | 1186 | 10 | 10 |
| | Avg | 10 | 9.9 |
| | SD | 0 | 0.3 |
| Untreated Controls | 1440 | 0 | 0 |
| | 1442 | 8 | 6 |
| | 1444 | 0 | 0 |
| | 1446 | 6 | 6 |
| | 1448 | 6 | 6 |
| | 1450 | 6 | 4 |
| | 1452 | 6 | 6 |
| | 1454 | 6 | 4 |
| | 1456 | 0 | 0 |
| | 1458 | 6 | 6 |
| | Avg | 4.40 | 3.80 |
| | SD | 2.94 | 2.60 |

Stakes treated with the test solution showed much less damage than untreated control stakes. The stakes in Newark, Del. were graded at 12 months. A summary of the results are given in Table 9 as averages of gradings at the Newark site, in comparison to the averages at the Starke site (from Table 8).

TABLE 9

Averages of decay and insect damage data for stakes treated with ammoniacal solution of ibuprofen, hydrolyzed octene/maleic anhydride copolymer and copper/tungstate complex and tested in Newark, DE, compared with Starke, FL results.

| Location | Treatment: Conc. In ppm | Time (Months) | Avg Decay | Avg. Insect damage |
|---|---|---|---|---|
| Starke, FL | Cu 1485/WO$_4$ 300/Ibuprofen 300/hydrolyzed OMA | 12 | 10 | 9.9 |
| | Cu 743/WO$_4$ 150/Ibuprofen 150/hydrolyzed OMA | 12 | 9.65 | 9.8 |
| | Cu 371/WO$_4$ 75/Ibuprofen 75/hydrolyzed OMA | 12 | 9.35 | 9.35 |
| | Control | 12 | 4.4 | 3.8 |
| Newark, DE | Cu 1485/WO$_4$ 300/Ibuprofen 300/hydrolyzed OMA | 12 | 10 | 10 |
| | Cu 743/WO$_4$ 150/Ibuprofen 150/hydrolyzed OMA | 12 | 9.95 | 10 |
| | Cu 371/WO$_4$ 75/Ibuprofen 75/hydrolyzed OMA | 12 | 9.85 | 9.9 |
| | Control | 12 | 8.8 | 9.75 |

With damage to controls extensive, strong protection by all treatment solutions was observed at the Starke, Fla. site. Since there was little decay and insect damage at the Newark site in 12 months, the differences between the treated and control stakes are small. It is expected that over longer periods of time, treated stakes will show less decay and insect damage with respect to controls at this site.

EXAMPLE 4

Ammoniacal Solution of Ibuprofen/Copper/Tungstate Complex and CE-Sorb6 amidoxime as Preservative A) Preparation of Ibuprofen/Copper/Tungstate Complex and CE-Sorb6

A solution of 116.7 g of copper sulfate pentahydrate, 7.98 g of sodium tungstate dihydrate, 6.64 g of sodium ibuprofen, 155 g of conc. ammonium hydroxide (57% ammonium hydroxide), and 250 g of water was prepared. To this was added 92.2 g of a 57% solution of the amidoxime of CE-Sorb6 having a DS=6.0 (prepared as described in General Methods). The mixture was stirred for 30 minutes at room temperature to prepare a concentrated wood preservation solution. The concentrated solution was then diluted to a final weight of 20 Kg with 1.4% aqueous ammonium hydroxide solution to prepare a wood preservation solution having 1485 ppm copper, 300 ppm ibuprofen, and 300 ppm tungstate ion.

B) Wood Preservation Treatment Procedure and Environmental Testing for Pre-Decay Stakes Treated with Ammoniacal Solution of Ibuprofen/Copper/Tungstate Complex and CE-Sorb6 amidoxime Ten stakes were prepared and treated with the solution prepared in Example 4A as described in Example 1B. The uptake of treatment solution was evident from the results given in Table 10.

TABLE 10

Penetration of Treatment Solution in SYP Pre-decay Stakes

| ID | Dry Wt (g) | Wet Wt (g) | Gross Retention (g) |
| --- | --- | --- | --- |
| W2119 | 233.29 | 450.13 | 216.84 |
| W2121 | 245.66 | 470.04 | 224.38 |
| W2123 | 245.64 | 468.11 | 222.47 |
| W2125 | 246.77 | 484.46 | 237.69 |
| W2127 | 240.22 | 470.31 | 230.09 |
| W2129 | 239.22 | 471.75 | 232.53 |
| W2131 | 239.87 | 476.4 | 236.53 |
| W2133 | 426.15 | 471.89 | 45.74 |
| W2135 | 232.6 | 474.7 | 242.1 |
| W2137 | 249.8 | 483.59 | 233.79 |

The 10 labeled stakes were cut to 45.7 cm (18") decay stake length, cutting from each end and leaving a 5.1 cm (2") witness section from the center of the stake. All witness sections were tested for copper penetration using the Chromazurol S test described in the General Methods. All witness sections tested turned dark blue indicating complete penetration of the wood by the wood preservative treatment solution.

Pre-decay stakes were similarly prepared and treated with 1:2 and 1:4 dilutions of the treatment solution prepared in Example 4A. Each 45.7 cm (18") stake was weighed, dimensioned and the results recorded. The group of 10 stakes from each half were bundled together and labeled for ground insertion at two separate test sites (Newark, Del. and Starke, Fla.). The bundles were stored in a cool area (AWPA Standard, Method E7-01, Sec. 7) until the stakes were installed in the ground. The stakes were placed in the ground as per AWPA E7-01. The positioning of the stakes was randomized in the test sites as per AWPA E7-01. After 12 months, the stakes in Starke, Fla. were removed from the ground and visually graded for decay and termite attack according to AWPA protocol E7-01. Stakes treated with ammoniacal solution of ibuprofen/copper/tungstate complex and CE-Sorb6 amidoxime prepared in Example 4A show less damage than controls as seen in the results in Table 11.

TABLE 11

Decay and insect damage data for Decay stakes treated with different dilutions of ammoniacal solution of ibuprofen/copper/tungstate complex and CE-Sorb6 amidoxime tested in Starke, FL.

| | | 12 mo scores | |
| --- | --- | --- | --- |
| Treatment | Stake ID | Decay | Insect damage |
| Copper(1485 ppm)/WO4(300 ppm/ Ibuprofen(300 ppm)/CE-Sorb6 amidoxime | 1168 | 10 | 10 |
| | 1170 | 10 | 10 |
| | 1172 | 10 | 10 |
| | 1174 | 10 | 9 |
| | 1176 | 10 | 10 |
| | 1178 | 10 | 10 |
| | 1180 | 10 | 10 |
| | 1182 | 10 | 10 |
| | 1184 | 10 | 10 |
| | 1186 | 10 | 10 |
| | Avg | 10 | 9.9 |
| | SD | 0 | 0.3 |
| Copper(742 ppm)/WO4(150 ppm)/ Ibuprofen(150 ppm)/CE-Sorb6 amidoxime | 1258 | 10 | 10 |
| | 1260 | 10 | 10 |
| | 1262 | 9.5 | 10 |
| | 1264 | 10 | 10 |
| | 1266 | 8 | 8 |
| | 1268 | 10 | 10 |
| | 1270 | 10 | 10 |
| | 1272 | 10 | 10 |
| | 1274 | 10 | 10 |
| | 1276 | 9 | 10 |
| | Avg | 9.65 | 9.8 |
| | SD | 0.63 | 0.6 |
| Copper(371 ppm)/WO4(75 ppm)/ Ibuprofen(75 ppm)/CE-Sorb6 amidoxime | 1278 | 10 | 10 |
| | 1280 | 9 | 10 |
| | 1282 | 10 | 10 |
| | 1284 | 9.5 | 9 |
| | 1286 | 8 | 7 |
| | 1288 | 10 | 10 |
| | 1290 | 8 | 10 |
| | 1292 | 9 | 10 |
| | 1294 | 10 | 8 |
| | 1296 | 10 | 9.5 |
| | Avg | 9.35 | 9.35 |
| | SD | 0.78 | 1.00 |
| Untreated Controls | 1440 | 0 | 0 |
| | 1442 | 8 | 6 |
| | 1444 | 0 | 0 |
| | 1446 | 6 | 6 |
| | 1448 | 6 | 6 |
| | 1450 | 6 | 4 |
| | 1452 | 6 | 6 |
| | 1454 | 6 | 4 |
| | 1456 | 0 | 0 |
| | 1458 | 6 | 6 |
| | Avg | 4.4 | 3.8 |
| | SD | 2.94 | 2.6 |

The stakes in Newark, Del. were also graded at 12 months. A summary of the results are given in Table 12 as averages of gradings, compared to the averages for the Starke site.

TABLE 12

Averages of decay and insect damage data for Decay stakes treated with different dilutions of ammoniacal solution of ibuprofen/copper/tungstate complex and CE-Sorb6 amidoxime tested in Newark, De and Starke, FL.

| Location | Treatment: Conc. in ppm | Time (Months) | Avg Decay | Avg Insect damage |
|---|---|---|---|---|
| Starke, FL | Cu 1485/WO$_4$ 300/Ibuprofen 300/CE-Sorb6 amidoxime | 12 | 10 | 9.9 |
|  | Cu 743/WO$_4$ 150/Ibuprofen 150/CE-Sorb6 amidoxime | 12 | 9.65 | 9.8 |
|  | Cu 371/WO$_4$ 75/Ibuprofen 75/CE-Sorb6 amidoxime | 12 | 9.35 | 9.35 |
|  | Control | 12 | 4.4 | 3.8 |
| Newark, DE | Cu 1485/WO$_4$ 300/Ibuprofen 300/CE-Sorb6 amidoxime | 12 | 10 | 9.9 |
|  | Cu 743/WO$_4$ 150/Ibuprofen 150/CE-Sorb6 amidoxime | 12 | 10 | 9.95 |
|  | Cu 371/WO$_4$ 75/Ibuprofen 75/CE-Sorb6 amidoxime | 12 | 9.8 | 9.95 |
|  | Control | 12 | 8.8 | 9.75 |

With decay and insect damage to controls extensive, strong protection by all treatment solutions was observed at the Starke, Fla. site. Since there was little decay and insect damage at the Newark site in 12 months, the differences between the treated and control stakes are small. It is expected that over longer periods of time, treated stakes will show less decay and insect damage with respect to controls at this site.

Preparation and Environmental Testing of Fahlstrom Stakes Treated with Ammoniacal solution of Ibuprofen/Copper/Tungstate Complex and CE-Sorb6 Selection and preparation of Fahlstrom stakes The following methods are based on AWPA Standard, Method E7-01, Sec. 4, 5, 6, and 7 and E11-97.

SYP boards, 3.175 cm×35.56 cm×243.84 cm (5/4"×14"×8 ft) and 3.175 cm×30.48 cm×243.84 cm (5/4"×12"×8 ft) were obtained from Delaware County Supply (Boothwin, Pa.). The boards were cut into Fahlstrom stakes of 4 mm×38 mm×254 cm (0.156"×1.5"×10") in size (AWPA Standard, Method E7-01, Sec 4.2, with the exception that the boards were milled without equilibration). The stakes were segregated by visual inspection (AWPA Standard, Method E7-01, Sec. 4.1) and stakes having knots, cracks, resin and sap pockets, signs of infection by mold, stain, and wood destroying fungi were eliminated. The remaining stakes were sorted into groups by weight (AWPA Standard, Method E7-01, Sec. 5). Stakes weighing between 20 g and 25 g were chosen for the imbibing experiment and placed in a controlled environment chamber at 23° C. and RH of 50% (Model 1-60LLVL Humidity Cabinet, Percival Scientific Inc., Boone, Iowa) for 21 days (AWPA Standard, Method E7-01, Sec. 4 and E11-97, Sec. 3). After equilibration in the environment chamber, each stake was identified by a painted number. Each stake was then weighed and dimensioned and the results recorded.

Treatment of the Fahlstrom stakes was carried out in a stainless steel pressure vessel designed and fabricated at the DuPont Experimental Station (Wilmington, Del.). Pressure was supplied by a Diaphragm Pump (Model S216J10; Sprague Products Div. of Curtiss-Wright Flow Control Corp., Brecksville, Ohio). The pressure vessel was constructed from sched. 80 SS pipe measuring 12.7 cm (5") diam. and was closed at each end with SS flanges and caps. The length of the pipe varied depending on the length of the wood to be treated. Typically, a 101.6 cm (40") length was chosen for treating 38"wood specimens. Other lengths of pipe were added via flanges to extend the length of the pressure vessel to accommodate 243.84 cm (8 ft) specimens or shorter lengths of pipe were used to treat 25.4 cm (10") specimens.

Batches of ten labeled stakes were loaded into a stainless steel separation rack (to simulate sticking, which is physical separation of lumber by placing small pieces of wood between boards to separate them, as well as two witness stakes (total 12 stakes), and placed in the pressure vessel. The pressure vessel was sealed and a vacuum of 69.85 cm Hg gauge (13.5 psig) was applied for a period of 30 minutes. The vacuum was broken by introduction of the imbibing fluid, the ammoniacal solution of ibuprofen/copper/tungstate complex and CE-Sorb6 prepared in Example 4A, to fill the pressure vessel and cover the wood. Air pockets were removed by circulating imbibing fluid through the vessel, and pressure of 7.18 kilopascal gauge (150 psig) was applied with a diaphragm pump for a period of 30 minutes. The pressure was released and the stakes allowed to equilibrate in the imbibing solution for 15 minutes. The pressure vessel was drained and the treatment rack bearing the stakes was removed. The stakes were lightly wiped with a paper towel and weighed. The Fahlstrom stakes gained weight in a manner similar to the stakes in Tables 1. and 3., which indicated that the ammoniacal solution of ibuprofen/copper/tungstate complex and CE-Sorb6 was successfully imbibed into the wood. Fahlstrom stakes were similarly treated with 1:2 and 1:4 dilutions of the treatment solution prepared in Example 4A.

The Fahlstrom stakes described were placed in the ground, along with untreated control stakes, at Hialeah, Fla., Starke, Fla., Newark, Del., and LaPlace, La. as per AWPA E7-01. The positioning of the stakes was randomized in the test sites as per AWPA E7-01. The stakes were evaluated for decay at 6 months vs. untreated control stakes according to AWPA standard E7-01. Results from the stakes in Hialeah are given in Table 13.

TABLE 13

Decay gradings of Fahlstrom stakes treated with ammoniacal solution of ibuprofen/copper/tungstate complex and CE-Sorb6 amidoxime at Hialeah, FL.

| Installed Feb. 2, 2006 Treatment | Stake ID | Aug. 1, 2006 6 mo decay |
|---|---|---|
| 1485 ppm Copper/300 ppm WO$_4$/300 ppm Ibuprofen/CE-Sorb6 amidoxime | 261-02 | 10 |
|  | 261-03 | 10 |
|  | 261-06 | 10 |
|  | 261-09 | 10 |
|  | 261-13 | 10 |
|  | 261-28 | 10 |
|  | 261-30 | 10 |
|  | 261-38 | 10 |
|  | 261-41 | 10 |
|  | 261-42 | 10 |
|  | Avg | 10 |
|  | SD | 0 |

TABLE 13-continued

Decay gradings of Fahlstrom stakes treated with ammoniacal solution of ibuprofen/copper/tungstate complex and CE-Sorb6 amidoxime at Hialeah, FL.

Installed Feb. 2, 2006

| Treatment | Stake ID | Aug. 1, 2006 6 mo decay |
|---|---|---|
| Copper (742 ppm)/WO$_4$ (150 ppm)/ Ibuprofen (150 ppm)/CE-Sorb6 amidoxime | 263-05 | 10 |
|  | 263-06 | 10 |
|  | 263-14 | 9.5 |
|  | 263-15 | 10 |
|  | 263-18 | 9 |
|  | 263-20 | 10 |
|  | 263-26 | 10 |
|  | 263-37 | 9 |
|  | 263-38 | 10 |
|  | 263-43 | 10 |
|  | Avg | 9.75 |
|  | SD | 0.40 |
| Copper (371 ppm)/WO$_4$ (75 ppm)/ Ibuprofen (75 ppm)/CE-Sorb6 amidoxime | 264-05 | 9 |
|  | 264-11 | 8 |
|  | 264-17 | 7 |
|  | 264-23 | 10 |
|  | 264-24 | 8 |
|  | 264-27 | 9.5 |
|  | 264-28 | 10 |
|  | 264-35 | 10 |
|  | 264-39 | 10 |
|  | 264-44 | 10 |
|  | Avg | 9.15 |
|  | SD | 1.05 |
| Untreated Controls | 275-01 | 8 |
|  | 275-04 | 7 |
|  | 275-05 | 7 |
|  | 275-07 | 6 |
|  | 275-08 | 8 |
|  | 275-11 | 6 |
|  | 275-13 | 7 |
|  | 275-15 | 6 |
|  | 275-18 | 8 |
|  | 275-20 | 8 |
|  | Avg | 7.1 |
|  | SD | 0.83 |

A summary of the results for 6 month gradings of the stakes at all four sites is given in Table 14 as averages of gradings at each site.

TABLE 14

Averages of decay and insect damage scores for Fahlstrom stakes treated with ammoniacal solution of ibuprofen/copper/tungstate complex and CE-Sorb6 amidoxime

| Location | Treatment:: Conc. in ppm | Time (Months) | Avg Decay | Avg Insect damage |
|---|---|---|---|---|
| Starke, FL | Cu 1485/WO$_4$ 300/Ibuprofen 300/ CE-Sorb6 amidoxime | 6 | 8.9 | 9.9 |
|  | Cu 743/WO$_4$ 150/Ibuprofen 150/ CE-Sorb6 | 6 | 7.7 | 10 |
|  | Cu 371/WO$_4$ 75/Ibuprofen 75/CE-Sorb6 amidoxime | 6 | 8.9 | 10 |
|  | Control | 6 | 9.2 | 9.2 |
| Newark, DE | Cu 1485/WO$_4$ 300/Ibuprofen 300/ CE-Sorb6 amidoxime | 6 | 10 | 10 |
|  | Cu 743/WO$_4$ 150/Ibuprofen 150/ CE-Sorb6 | 6 | 10 | 10 |
|  | Cu 371/WO$_4$ 75/Ibuprofen 75/CE-Sorb6 amidoxime | 6 | 10 | 10 |
|  | Control | 6 | 7.9 | 9.3 |
| Hialeah, FL | Cu 1485/WO$_4$ 300/Ibuprofen 300/ CE-Sorb6 amidoxime | 6 | 10 | xxxx |
|  | Cu 743/WO$_4$ 150/Ibuprofen 150/ CE-Sorb6 amidoxime | 6 | 9.75 | xxxx |
|  | Cu 371/WO$_4$ 75/Ibuprofen 75/CE-Sorb6 amidoxime | 6 | 9.15 | xxxx |
|  | Control | 6 | 7.1 | xxxx |
| LaPlace, LA | Cu 1485/WO$_4$ 300/Ibuprofen 300/ CE-Sorb6 amidoxime | 7 | 9.9 | 10 |
|  | Cu 743/WO$_4$ 150/Ibuprofen 150/ CE-Sorb6 amidoxime | 7 | 9.7 | 10 |
|  | Cu 371/WO$_4$ 75/Ibuprofen 75/CE-Sorb6 amidoxime | 7 | 9.2 | 10 |
|  | Control | 7 | 8.9 | 9.9 | xxxx means no insect damage observed at this site

Protection from decay was observed for all treatments at the Hialeah site. It is expected that over longer periods of time, treated Fahlstrom stakes will show less decay and insect damage with respect to controls at the additional testing sites

What is claimed is:

1. An aqueous composition comprising in admixture (a) a complex comprising (i) ibuprofen, and (ii) copper ions, zinc ions or a mixture thereof; and (b) ammonia and/or ethanolamine; wherein component (b) is present in an amount sufficient to solubilize the complex.

2. The composition of claim 1 which further comprises a component (c) selected from one or both of an additional antifungal component and an additional termiticidal component.

3. The composition of claim 2 wherein the component (c) comprises molybdate ions, tungstate ions, a tropolone, or mixtures thereof.

4. The composition of claim 1 further comprising at least one hydrolyzed olefin/maleic anhydride copolymer.

5. The composition of claim 4 wherein the copolymer is hydrolyzed octene/maleic anhydride copolymer, hydrolyzed styrene/maleic anhydride copolymer, or mixtures thereof.

6. The composition of claim 1 further comprising a copper chelating compound comprising at least two functional groups selected from the group consisting of amidoxime, hydroxamic acid, thiohydroxamic acid, N-hydroxyurea, N-hydroxycarbamate, and N-nitroso-alkyl-hydroxylamine.

7. The composition of claim 6 wherein the chelating compound comprises at least two hydroxamic groups and the chelating compound is derived from styrene/maleic anhydride or octene/maleic anhydride.

8. The composition of claim 6 wherein the chelating compound comprises at least two functional groups selected from amidoxime and hydroxamic acid, and the amidoxime or hydroxamic acid is derived from a cyanoethylated compound.

9. The composition of claim 8 wherein the cyanoethylated compound is derived from the cyanoethylation of a primary amine, a secondary amine, blood albumin, casein, soybean protein, wool, or corn zein; or from materials derived from blood albumin, casein, gelatin, gluten, soybean protein, wool, or corn zein.

10. The composition of claim 8 wherein the cyanoethylated compound is derived from the cyanoethylation of synthetic polymers selected from the group consisting of acetone-formaldehyde condensate, acetone-isobutyraldehyde condensate, methyl ethyl ketone-formaldehyde condensate, poly(allyl alcohol), poly(crotyl alcohol), poly(3-chloroallyl alcohol), ethylene carbon monoxide copolymers, polyketone from propylene, ethylene and carbon monoxide, poly(methallyl alcohol), poly(methyl vinyl ketone), and poly(vinyl alcohol).

11. The composition of claim 8 wherein the cyanoethylated compound is obtained from the cyanoethylation of materials selected from the group of: alcohols, carbohydrates, dextran, dextrin, gums, starches, modified natural polymers; and compounds derived from natural polymers.

12. The composition of claim 8 wherein the cyanoethylated compound is obtained from the cyanoethylation of sucrose or sorbitol.

13. A process for preserving cellulosic material, or an article that comprises cellulosic material, comprising contacting the cellulosic material or article with the composition of claim 1.

14. The process of claim 13 wherein the cellulosic material is selected from the group consisting of wood, lumber, plywood, oriented strand board, cellulose, hemicellulose, lignin, cotton and paper.

15. The process of claim 13 which comprises dipping, brushing, spraying, draw-coating, rolling, or pressure-treating the cellulosic material or article with the composition of claim 1.

16. The process of claim 13 wherein the cellulosic material is wood or lumber.

17. The process of claim 16 further comprising subjecting the wood or lumber to a vacuum before and/or after it is contacted with the composition of claim 1.

18. The process of claim 13 further comprising a step of incorporating the cellulosic material or the article into a structure or into a consumable device.

19. Cellulosic material, or an article comprising a cellulosic material, wherein the composition of claim 1 is adsorbed on and/or absorbed in the cellulosic material.

20. The material or article of claim 19 wherein the cellulosic material is selected from the group consisting of wood, paper, cellulose, cotton, lignin, and hemicellulose.

21. The material or article of claim 19 wherein the cellulosic material is selected from the group consisting of wood, lumber, plywood, oriented strand board, paper, cellulose, cotton, lignin and hemicellulose; and the composition further comprises an ibuprofen—copper and/or zinc ion complex.

22. The material or article of claim 19 wherein the composition further comprises a tungstate and/or molybdate ion—copper and/or zinc ion complex.

23. The material or article of claim 19 wherein the composition further comprises a hydrolyzed olefin/maleic anhydride copolymer.

24. The material or article of claim 19 wherein the composition further comprises a copper chelating compound comprising at least two functional groups selected from the group consisting of amidoxime, hydroxamic acid, thiohydroxamic acid, N-hydroxyurea, N-hydroxycarbamate, and N-nitroso-alkyl-hydroxylamine.

25. The material or article of claim 24 wherein the chelating compound comprises at least two hydroxamic groups and is derived from styrene/maleic anhydride or octene/maleic anhydride.

26. The material or article of claim 24 wherein the chelating compound comprises at least two functional groups selected from amidoxime and hydroxamic acid, and the amidoxime or hydroxamic acid is derived from a cyanoethylated compound.

27. The material or article of claim 26 wherein the cyanoethylated compound is obtained from the cyanoethylation of sucrose or sorbitol.

28. A structure or consumable device comprising the cellulosic material or article of claim 19.

* * * * *